(12) United States Patent
Tourrel et al.

(10) Patent No.: US 9,656,065 B2
(45) Date of Patent: May 23, 2017

(54) IMPLANTABLE DEVICE WITH REMOVABLE MAGNET

(71) Applicant: Oticon Medical A/S, Smørum (DK)

(72) Inventors: Guillaume Tourrel, Vallauris (FR); Hervé Ibanez, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 452 days.

(21) Appl. No.: 14/468,690

(22) Filed: Aug. 26, 2014

(65) Prior Publication Data

US 2015/0087892 A1 Mar. 26, 2015

(30) Foreign Application Priority Data

Sep. 26, 2013 (EP) .................................... 13186200

(51) Int. Cl.
*H04R 25/00* (2006.01)
*A61N 1/08* (2006.01)
*A61N 1/36* (2006.01)
*A61N 1/372* (2006.01)
*A61N 1/375* (2006.01)

(52) U.S. Cl.
CPC ........... *A61N 1/08* (2013.01); *A61N 1/36032* (2013.01); *A61N 1/375* (2013.01); *A61N 1/37223* (2013.01)

(58) Field of Classification Search
CPC .. A61N 1/08; A61N 1/36032; A61N 1/37223; A61N 1/375; H04R 25/00; H04R 25/60; H04R 25/65
USPC ......................................................... 600/25
See application file for complete search history.

(56) References Cited

U.S. PATENT DOCUMENTS

2009/0099403 A1   4/2009   Zimmerling et al.
2009/0287278 A1   11/2009  Charvin

FOREIGN PATENT DOCUMENTS

WO   WO 2008/109800 A1   9/2008
WO   WO 2013/043176 A1   3/2013

*Primary Examiner* — John Lacyk
(74) *Attorney, Agent, or Firm* — Birch, Stewart, Kolasch & Birch, LLP

(57) ABSTRACT

A cochlear implant system includes a subcutaneous housing which includes a main body and a bottom cover secured to the main body. A central cavity in a center of the subcutaneous housing is formed by a portion of an outer surface of the main body. A magnet is removably inserted into the central cavity and includes a cylindrical body with a central axis aligned with a removal axis of the central cavity, a groove extending circumferentially around the cylindrical body, and a top surface, which includes an outer edge, a plurality of ribs extending radially farther than the outer edge, and a plurality of abutments extending radially farther than the ribs. A compressive ring is seated in the groove of the cylindrical body and engages under a ledge in the central cavity when the magnet is inserted into the central cavity and biases the magnet against removal from the central cavity.

14 Claims, 10 Drawing Sheets

IMPLANTABLE DEVICE WITH REMOVABLE MAGNET

TECHNICAL FIELD

The technical field relates to insertion, positioning, and securing of a magnet in an implanted part of a cochlear implant and an associated tool for its removal.

BACKGROUND

Cochlear implants typically include an external device that is coupled to an implanted device. The coupling may be achieved through electromagnetic coupling, where coils transmit and/or receive information and/or energy. Consequently, external and internal devices each utilize a coil to transmit and to receive information and/or energy. The external device includes at least one coil and the internal device includes at least one coil.

In order to align the coils of the external device and the internal device with respect to each other, one or more magnets are associated each coil. Thus, the two coils are aligned and the external device is pulled toward the implanted device by the magnets. The external device is thus held in the proper working position on top of the implanted device by magnetic force.

The magnet of the implanted device may be encapsulated in a biocompatible housing to ensure compatibility with the body of the user in case the magnet is made of magnetic material that is itself not biocompatible. As shown is FIG. 1A, generally the magnet 13 is mounted into a small hermetical part that is made of silicone, because silicone is biocompatible. To position this magnet under the skin in the correct position, the magnet 13 is inserted into a hole included in the silicone part 14, in the center of the coil 12.

As shown on FIG. 1B, in a different design, fixed magnet 104 is permanently installed into the hermetic housing 101 made of ceramic 105 and titanium 106, in the center of coil 103. Fixed magnet 104 is considered to be non-removable due to the way it is installed in the hermetic housing 101.

Most of the time, cochlear implants are compatible with low power magnetic resonance imaging (MRI) up to magnetic field strength of 1.5 tesla (T). At levels up to 1.5 T an implant is generally secure, minimal heat is generated, the magnetic characteristics of the implanted magnet remain stable, any artifact effects in the MRI are acceptable, and the implanted device is not displaced.

However, when higher power MRI has to be performed on patients wearing a cochlear implant, some problems can occur, including demagnetization of the implanted magnet, strong force applied to tissues due to the magnetic field of the MRI interacting with the internal magnet, heat generation, and undesirable artifacts in the MRI results.

To address these concerns, some cochlear implants are designed to enable removal magnets while the cochlear implant remains implanted in the user. The removal of the implanted magnet enables the use of high power MRI. As shown in FIG. 1C, a magnet 503 is placed in the center of silicone molding 504, where silicone lips 507 partially cover the top of the magnet 503. A central hole and slots 508 between silicone lips 507 enable the removal of the magnet by deforming the silicone lips 507 when force is applied to the magnet 503.

While the design in FIG. 1C enables removal of the magnet 503, the design does not provide sufficiently high stability for the magnet 503 when it is installed in the cochlear implant due to the elasticity of silicone. Further, when the magnet 503 is removed and replaced, it may be misaligned and have a secondary displacement due to torque. Furthermore, the design provides no specific solution to make the handling and removal of the magnet 503 easy for the healthcare provider.

From EP2119474A2 it is known to provide the magnet in a releasable manner placed in a hole centered in a circular ceramic housing. The ceramic housing thus encircles the magnet. The document does not provide information on measures to facilitate the fast removal and replacement of the magnet.

SUMMARY

The solution proposed in the disclosure resolves shortcomings noted above by providing a stable mounting solution for a magnet and a tool for its removal. Further, the solution is minimally invasive using a compact structure. The proposed solution takes into account specific tooling needed by a surgeon in order to grasp and remove a magnet from the surrounding housing.

In an embodiment, a cochlear implant system includes a subcutaneous housing containing electronics for at least stimulation or collection of data and at least one antenna for communicating with an external device. The subcutaneous housing includes a main body having a U-shaped radial cross-section, a bottom cover secured to the main body, forming a hollow cavity bounded by an inner surface of the main body and the bottom cover, and a central cavity in a center of the subcutaneous housing formed by a portion of an outer surface of the main body. A magnet is removably inserted into the central cavity, the magnet including a cylindrical body with a central axis, the central axis aligned with a removal axis of the central cavity, a groove extending circumferentially around the cylindrical body, and a top surface. The top surface includes an outer edge, a plurality of ribs extending radially farther than the outer edge, and a plurality of abutments extending radially farther than the ribs. Further, a compressive ring is seated in the groove of the cylindrical body, wherein the compressive ring engages under a ledge in the central cavity when the magnet is inserted into the central cavity and biases the magnet against removal from the central cavity.

In an embodiment, the cochlear implant system further includes a silicone rim surrounding the body and tapering radially outward.

In an embodiment, the silicone rim includes two flaps extending outward, each flap including a support ring configured to accept a bone anchoring screw.

In an embodiment, the cochlear implant system further includes a junction area formed as a part of the silicone rim between the two flaps, the junction area accommodating electrodes passing to the cochlear implant.

In an embodiment, the bottom cover is a stamped titanium cover.

In an embodiment, the stamped titanium cover includes a plurality of feedthroughs.

In an embodiment, the main body is made of a biocompatible ceramic material.

In an embodiment, the biocompatible material is one of zirconia toughened alumina, high purity alumina, and pure zirconia.

In an embodiment, the top surface of the magnet includes three ribs and three abutments equally spaced around the outer circumference of the outer edge of the top surface, the abutments are in contact with a rim of the central cavity when the magnet is fully inserted into the central cavity, and the ribs are not in contact with the rim of the central cavity.

In an embodiment, each rib has a smoothly tapered edge connected to the outer edge of the top surface, and a void is bounded by the outer edge of the top surface and the rim of the central cavity.

In an embodiment, the cochlear implant system further includes a tool for removing the magnet from the central cavity, the tool including a handle portion, a second magnet installed on a first end of the handle portion, three blades extending from the first end parallel to a central axis of the handle portion, each blade terminating with a hook, wherein each blade is insertable in the void, each hook engages under a respective rib when the handle portion is rotated after insertion of the blades, and the second magnet attracts the magnet in the central cavity when the hooks engage under the ribs.

In an embodiment, the magnet includes an outer casing made of a biocompatible material, and a magnetic core.

DETAILED DESCRIPTION

Embodiments of the present disclosure retain a cochlear implant magnet securely positioned in the center of the cochlear implant housing while maintaining a very compact structure. At the same time, the electronics and the coil of the cochlear implant are hermetically isolated. An interface between the magnet assembly and the cochlear housing has been designed to provide excellent alignment of the magnet within the cochlear implant housing. The interface also enables easy and safe removal of the magnet when needed.

Figure 1A:
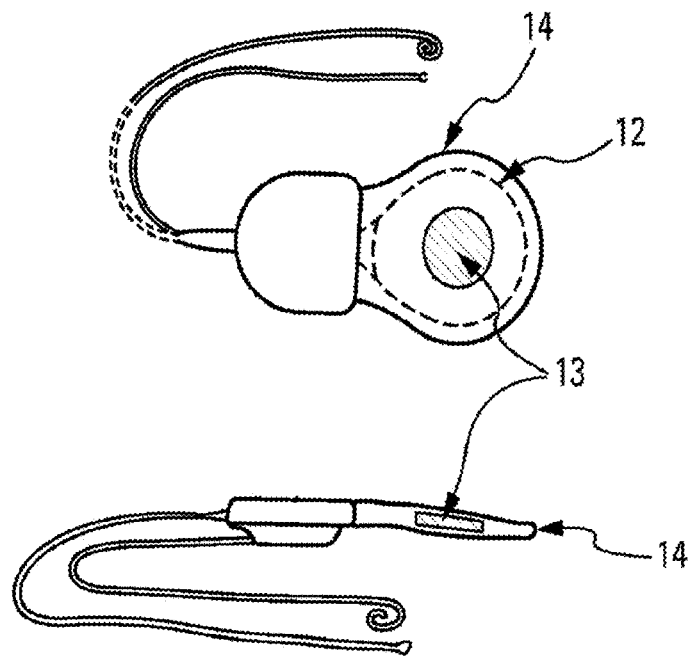
FIG. 1A illustrates a top and a side view of a cochlear implant housing according to background art.
Figure 1B:
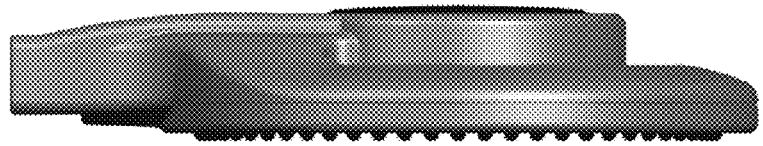
FIG. 1B illustrates a partial cross section view of a cochlear implant composed of a hermetic housing with a non-removable magnet according to background art.
Figure 1B:
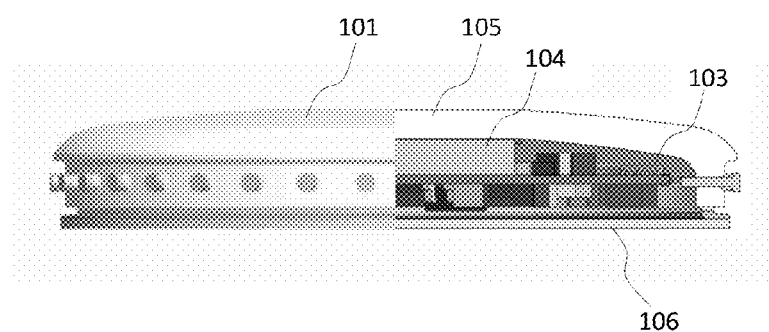
Figure 1C:
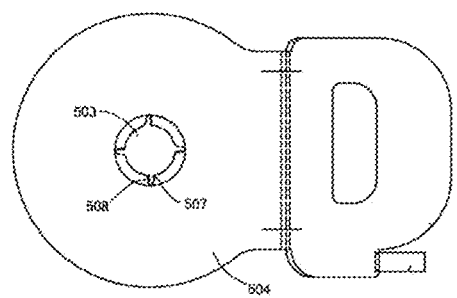
FIG. 1C illustrates a top view of a cochlear implant housing according to background art.
Figure 2A:
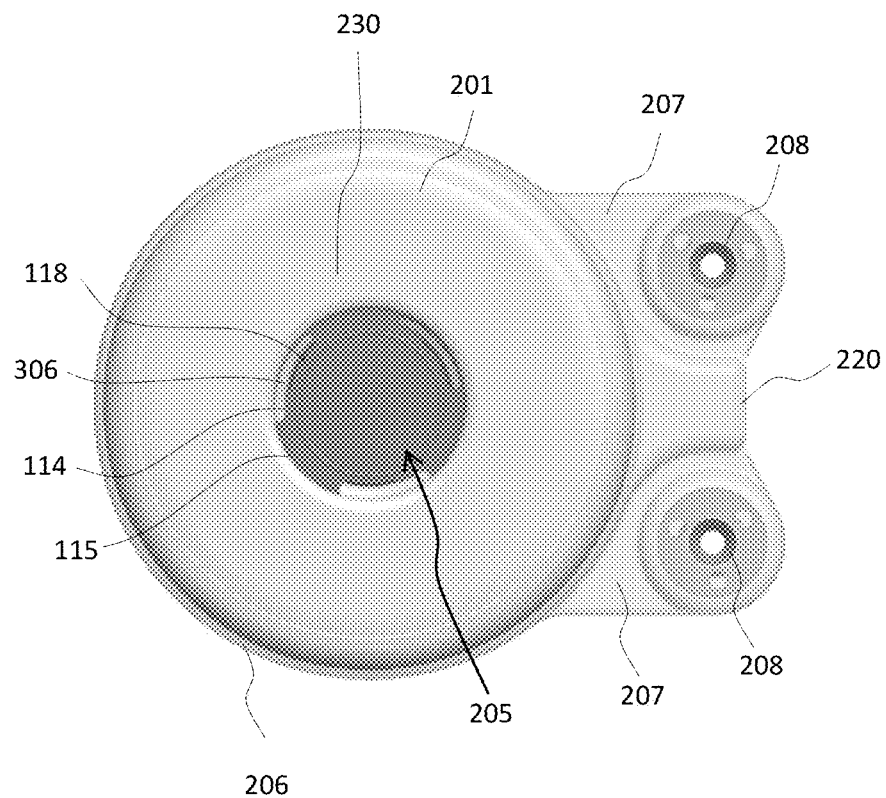
FIGS. 2A and 2B illustrate a front view and a cross section view of an example of a cochlear implant with a removable magnet according to an embodiment of the disclosure.
Figure 2B:
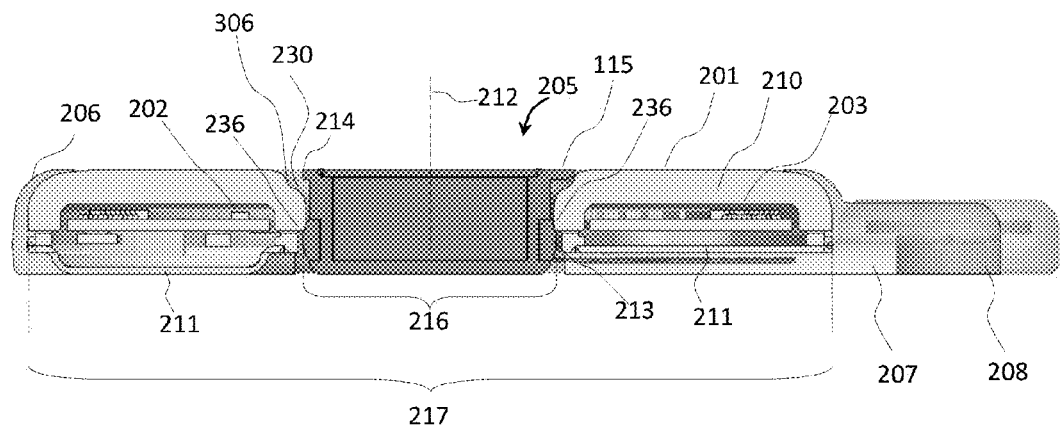

FIGS. 2A-B illustrate an example of a cochlear implant with a subcutaneous housing 201 which has a compact structure and houses electronics 202 and one or more coils 203 for receiving and transmitting information and energy. Also feedthroughs (not shown) for connecting electrodes to the subcutaneous housing are part of the construction. Such electrodes can stimulate or measure electrophysiological signals in the patient's body. In other situations, the electrical connections to/from the inside of the housing may also or alternatively connect an electromechanical actuator such as vibrator for bone conduction or for stimulating the middle ear.

A magnet 205 is installed removably in a central cavity 230 of housing 201. The central cavity 230 is in the center of the annulus formed by the housing 201. The magnet 205 creates a magnetic field that holds and centers an external device that includes one or more coils. The external device can thus communicate with the implanted cochlear implant or supply energy to the cochlear implant.

The subcutaneous housing 201 may include a silicone rim 206 to provide a soft and ergonomic shape that helps preserve surrounding patient tissues when the cochlear implant is surgically implanted. The continuation of the silicone rim 206 forms two flaps 207. Flaps 207 each include a reinforcing ring 208. The rings 208 can be made of biocompatible material such as titanium, PEEK or PEKK, in order to allow the implant to be fixed onto the temporal bone of a patient. The implant can be fastened to the skull bone with screws that pass through rings 208.

An area between reinforcing rings 208 forms a junction 220. The junction 220 can house or accommodate electrodes passing to feedthroughs from an external device.

The main housing 201 is composed of a main body having a U-shaped cross sectional profile, referred to as U-shaped main body 210. The U-shaped main body 210 forms a cavity which hermetically accommodates electronics 202 and coil 203. The U-shaped main body 210 can be made of biocompatible ceramic such as zirconia toughened alumina, high purity alumina, or pure zirconia. A stamped titanium cover 211 is attached to the rim of the U-shaped main body 210 by laser welding to form a hermetically sealed cavity.

Magnet 205 is guided directly by U-shaped main body 210 through a precisely sized diameter of central cavity 230. The precise sizing of the diameter reduces free movement of the magnet 205 to only a rotation about removal axis 212 or a translation in the direction of the removal axis 212. No pitching or tilting of magnet 205 relative to housing 201 is possible when the magnet is fully installed in the central cavity 230. Removal axis 212 passes through the center of the central cavity 230 and is perpendicular to the plane of the top surface of main body 210.

The magnet 205 is preferably biocompatible. Thus, the magnet 205 may be constructed as a magnetic core 240 surrounded by a biocompatible housing 245. The biocompatible housing 245 thus forms the outer surface of the magnet 205 and may be made of titanium.

Figure 2C:
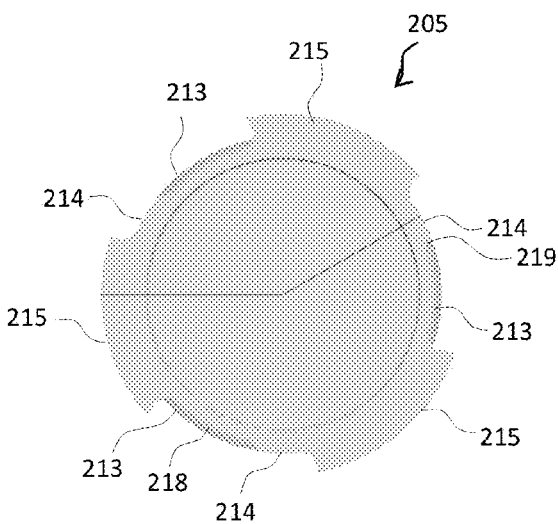
FIG. 2C illustrates a top view and a cross sectional view of an example of a removable magnet assembly according to an embodiment of the disclosure.
Figure 2C:
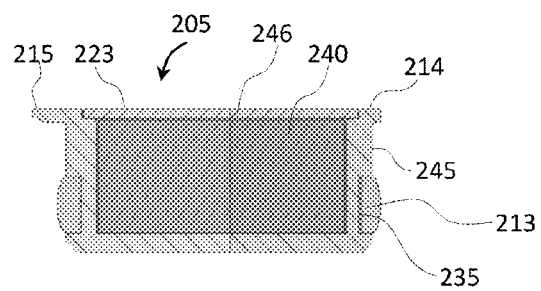

As illustrated in FIG. 2C, the body of magnet 205 is radially symmetrical except for a portion at the top surface 223 of the magnet 205. The top of the magnet 205 has an outer edge 218 which is radially surpassed by raised ribs 214 and abutments 215. FIG. 2C illustrates an example with three ribs 214 and three abutments 215.

Abutments 215 extend radially farther out beyond the edge of the ribs 214. The abutments 215 prevent the magnet 205 from passing completely through the central cavity 230 of the housing 201, and in case of shock or impact directly on the removable magnet 205, energy will be dissipated to the housing 201 and will not impact the patient's temporal bone by the small surface 216 of the removable magnet 205, but by the entire surface 217 of the implant housing 212.

While abutments 215 are in contact with the rim of the central cavity 230, the ribs 214 are sized smaller than the abutments 215, so there is a gap 306 between the edge of ribs 214 and the rim of the central cavity. This gap 306 allows the insertion of a tool 303 to remove the magnet 205 as described below. The ribs 214 have a smooth transition 219 from the edge 218, facilitating the rotation of tool 303 after it is inserted.

Magnet 205 includes a silicone ring 213 that is calibrated to withstand a force induced by RMI of up to 3T. The silicone ring 213 is placed in a radial groove 235 in the body of magnet 205. When the magnet 205 is inserted into central cavity 230, the silicone ring 213 exerts force on both the magnet 205 and the inner walls of central cavity 230 to hold the magnet 205 securely in place. As shown in FIG. 2B, the side profile of central cavity 230 has a ledge 236 under which silicone ring 213 is engaged, thus biasing the magnet 205 against removal from the central cavity 230.

Figure 3A:
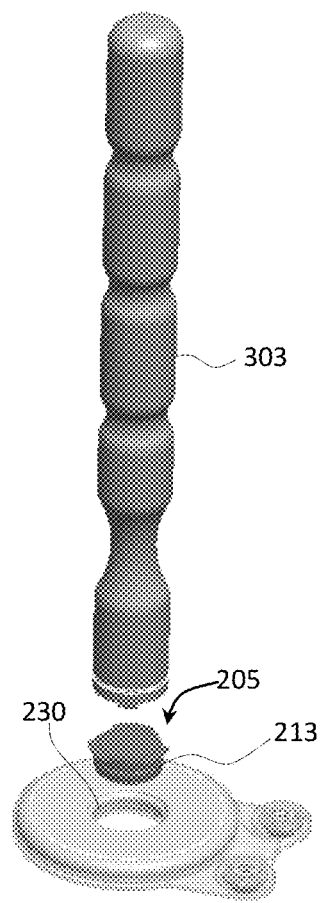
FIG. 3A illustrates a perspective view of an example of cochlear implant with its magnet removed with a tool according to an embodiment of the disclosure.

As shown in FIG. 3A, magnet 205 can be removed from the housing 302 with removal tool 303. It may sometimes be necessary to remove the magnet 205, such as when a very high level of MRI (e.g., above 3T) is needed.

Figure 3B:
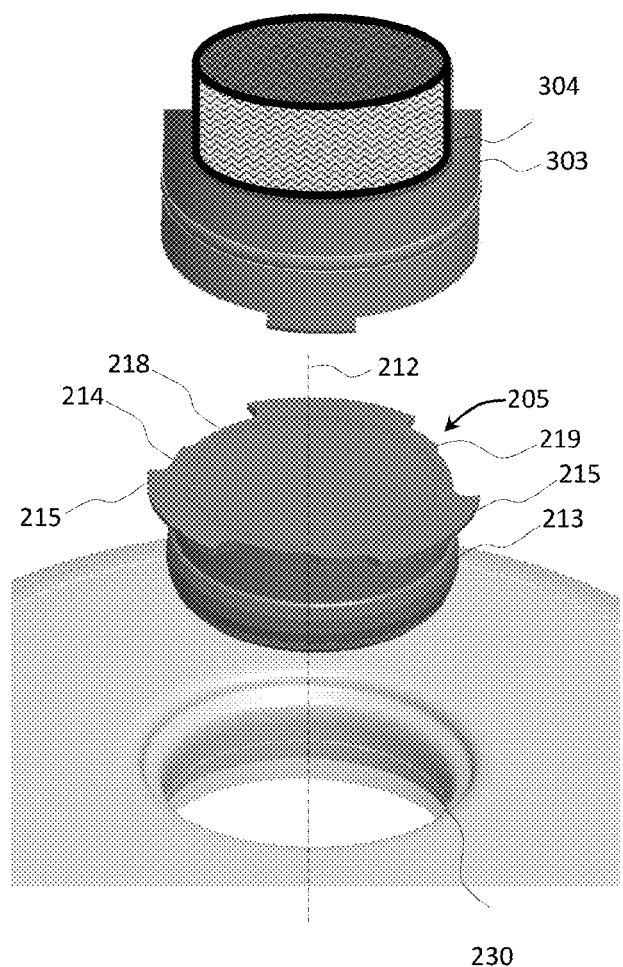
FIG. 3B illustrates a detailed perspective view of an example of cochlear implant with its magnet removed from its place according to an embodiment of the disclosure.
Figure 3C:
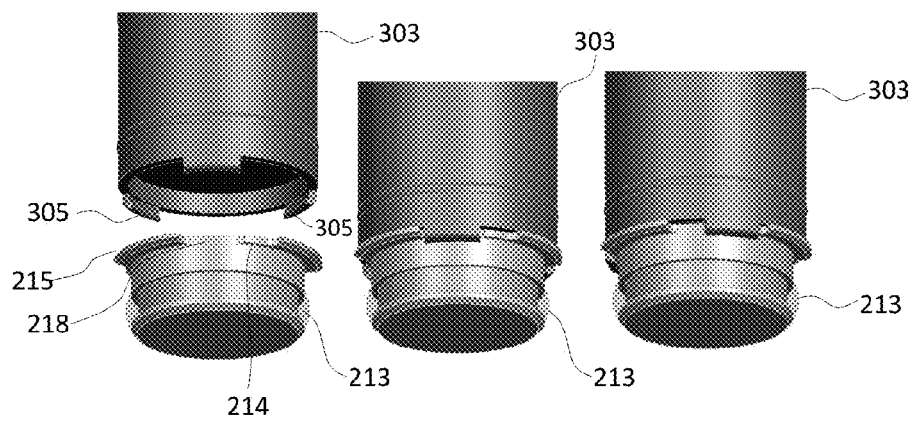
FIG. 3C illustrates various stages of interaction between removal tool and magnet.

When the magnet is to be removed, a surgeon can make an incision above the magnet and lift the skin away from the magnet area. A tool 303 can then be inserted through the incision and used to remove the magnet 205. As shown in detail in FIG. 3B, the tool 303 has its own magnet 304 placed at the proximal edge of the tool in order to automatically align the tool 303 on the magnet 205. As seen in FIG. 3C the surgeon has to insert the number of blades 305 at the proximal edge of the tool 303 into the gaps 306 defined between the outer edge of the magnet 218 and the rim of the central cavity 230. This position is seen in the middle part of FIG. 3C. Then, the tool 303 is turned counter-clockwise enough to lock the blades 305 under the ribs 214 via hooks 310. This final position is shown in the left hand view of FIG. 3C. In this position a secure engagement between tool and magnet has been established, and the tool and magnet may be lifted out of cavity 230 without further ado. As the surgeon exerts force on the magnet, the supporting force from the silicone ring 213, which holds the magnet 205 in the cavity 230, is overcome and the magnet is removed. The embedded magnet 304 holds the magnet 205 at the proximal edge of the tool 303 even after the magnet 205 is removed. The magnet 205 can be easily removed from the tool by hand if need be, and be dealt with in the usual flow of contaminated elements of the hospital.

A new sterile magnet 205 may be put in place by hand, without using a tool. It is preferable to rinse and dry the central cavity 230 before installing the new magnet 205. As the surgeon presses the new magnet 205 into cavity 230, compression strength of the silicone ring 213 on the new magnet 205 is overcome, and the magnet 205 slides securely into its correct position.

Figure 2D:
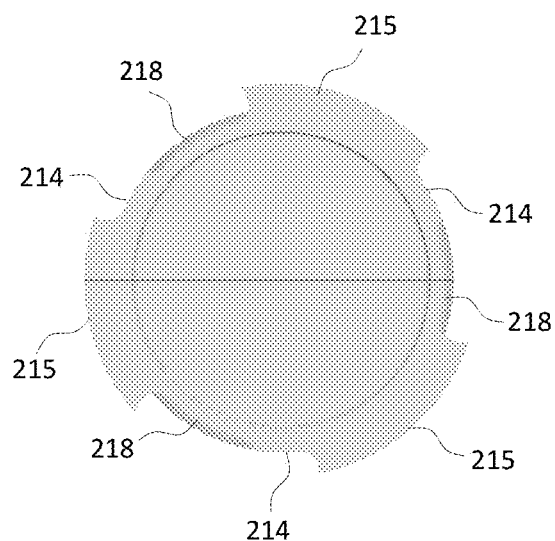
FIG. 2D illustrates a further top view and cross sectional view of a further example of the dislosure.
Figure 2D:
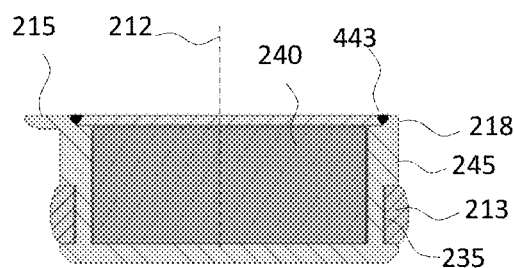
Figure 4:
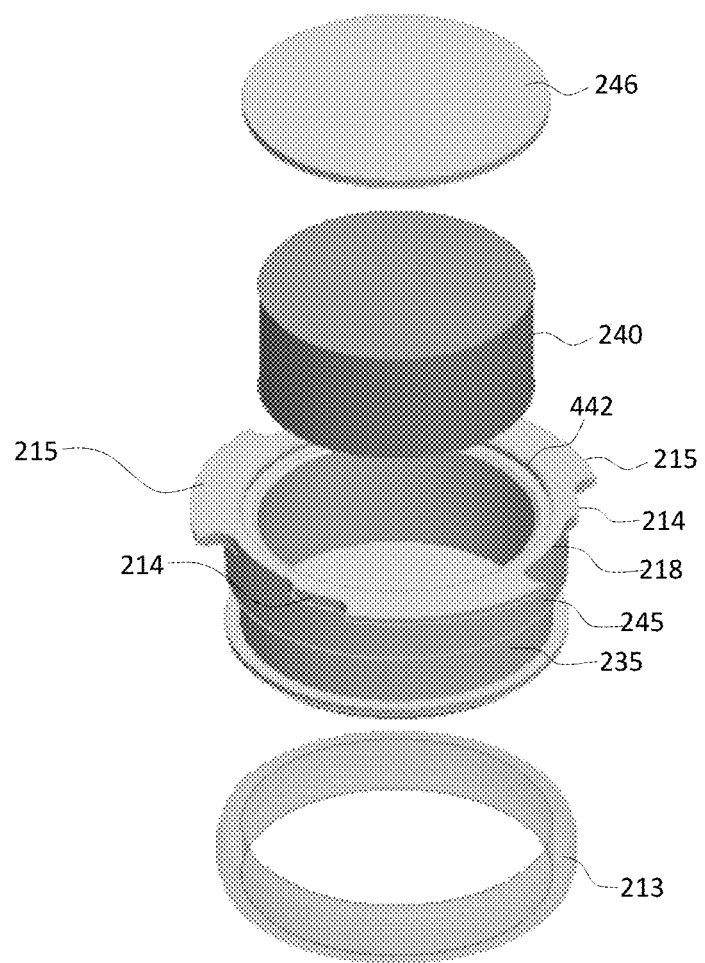
FIG. 4 shows an exploded view of a magnet and magnet holder according to the disclosure.

FIG. 4 discloses an exploded view of the magnet and its enclosure. The enclosure comprises a biocompatible housing 245 shaped as a bucket with an outwardly directed upper rim comprising the outer edge 218, raised ribs 214 and abutments 215. A lid 246 is provided and secured to the biocompatible housing 245 in a top recess 442, and in FIG. 2D a weld line 243 is indicated for the fusing of lid 246 and biocompatible housing 245. Other ways of fusing the lid to the housing could be used such as gluing or brazing. The various raised ribs 214 and abutments 215 are in the disclosed embodiment made as part of the housing 245, but the skilled person would know, that there are many other options, such as providing these structural details as part of the lid.

Figure 5A:
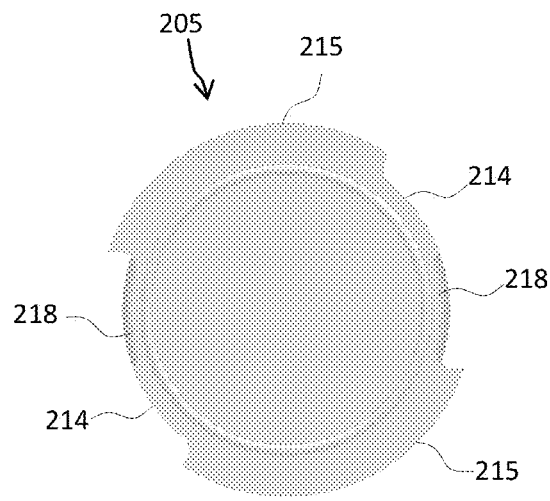
FIG. 5A is a plane view of a further embodiment of the disclosure.
Figure 5B:
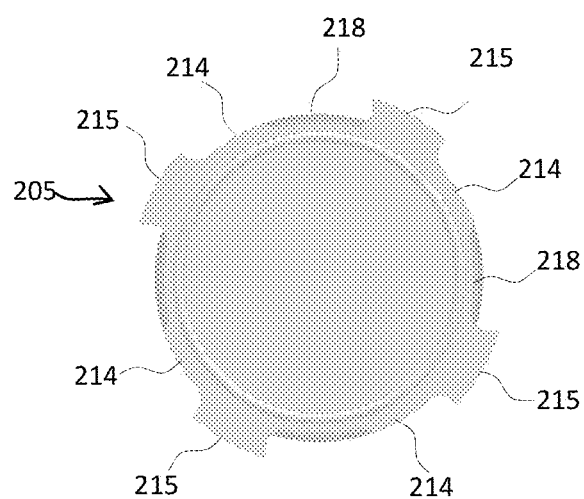
FIG. 5B is a plane view of yet another embodiment of the disclosure.

FIGS. 5A and 5B discloses embodiments with two or four abutments 215 respectively dispersed evenly around the circumference of the magnet 205 and a commensurate number of ribs 214.

Figure 6A:
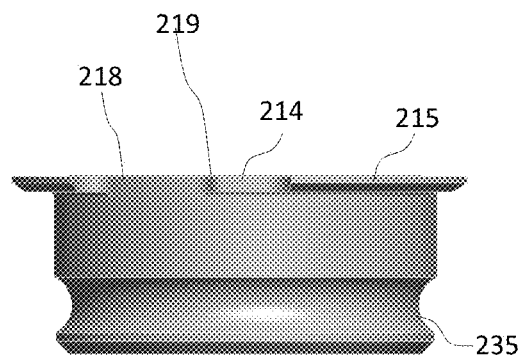
FIG. 6A discloses a further embodiment of the disclosure in two plane views.
Figure 6A:
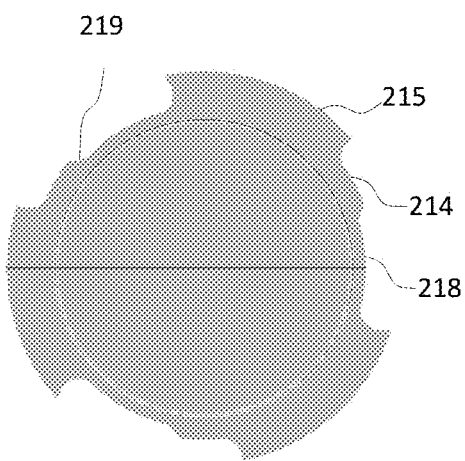
Figure 6B:
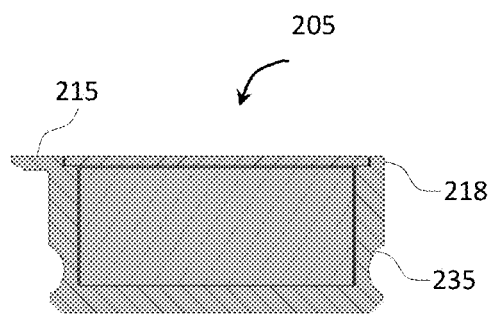
FIG. 6B is a cross sectional view of the embodiment of FIG. 6A.
Figure 6C:
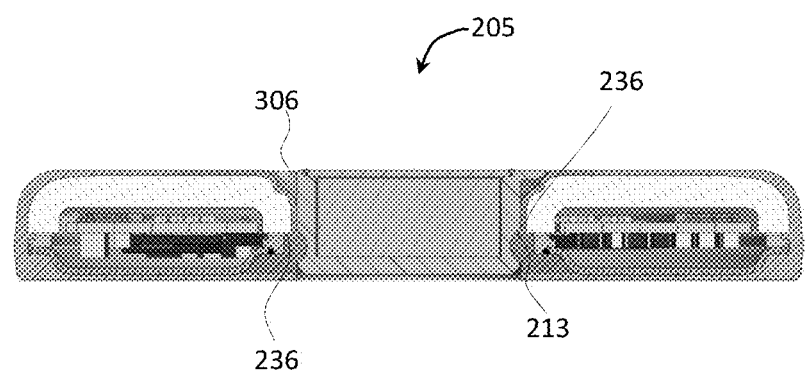
FIG. 6C is a cross sectional view of the housing belonging to the embodiment of FIG. 6A and 6B.

In FIG. 6A, B and C a further embodiment is shown wherein the silicone ring 213 is provided as part of the implant, and the magnet 205 simply comprises the groove 235. When the magnet is lifted out of the implant the silicone ring 213 stays with the implant. This is advantageus from a hygienic point of view, as the intersection between silicone ring and magnet groove will not lend itself as a hiding place for infecting agents during or after autoclaving.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

List of Elements

Number Element
12 coil
13 magnet
14 silicone part
101 hermetic housing
103 coil
104 fixed magnet
105 ceramic
106 titanium
201 subcutaneous housing
202 electronics
203 coil(s)
204 feedthroughs
205 magnet
206 silicone rim
207 flaps
208 ring
209 axis
210 U-shaped main body
211 stamped titanium cover
212 removal axis
213 silicone ring
214 rib
215 abutment
216 bottom surface of magnet
217 surface of housing
218 outer edge of magnet top
219 transistion
220 junction
223 top surface of magnet
230 central cavity
235 groove
236 ledge
240 magnetic core
242 top recess
243 weldline
245 biocompatible housing
246 lid
303 removal tool
304 magnet in tool 305 blade
306 gap(s)
310 hook
503 magnet
504 silicone molding
507 silicone lips
508 slots

The invention claimed is:

1. A cochlear implant system, comprising:
a subcutaneous housing containing electronics for at least stimulation or collection of data and at least one antenna for communicating with an external device, the subcutaneous housing including
a main body having a U-shaped radial cross-section,
a bottom cover secured to the main body, forming a hollow cavity bounded by an inner surface of the main body and the bottom cover, and
a central cavity in a center of the subcutaneous housing formed by a portion of an outer surface of the main body and
a ledge in the central cavity;
a magnet removably inserted into said central cavity, the magnet including
a cylindrical body with a central axis, the central axis aligned with a removal axis of the central cavity,
a groove extending circumferentially around the cylindrical body, and
a top surface, the top surface including
an outer edge,
a plurality of ribs extending radially farther than the outer edge, and
a plurality of abutments extending radially farther than the ribs; and
a compressive ring seated in at least one of the groove of the cylindrical body or in the ledge in the central cavity, wherein
the compressive ring engages the groove and below the ledge when the magnet is inserted into the central cavity and biases the magnet against removal from the central cavity.

2. The cochlear implant system according to claim 1, further comprising:
a silicone rim surrounding the body and tapering radially outward.

3. The cochlear implant system according to claim 2, wherein
the silicone rim includes two flaps extending outward, each flap including a support ring configured to accept a bone anchoring screw.

4. The cochlear implant system according to claim 3, further comprising:
a junction area formed as a part of the silicone rim between the two flaps, the junction area accommodating electrodes passing to external transducers such as cochlear, ear nerve or brain stem electrodes, or cochlear vibrators.

5. The cochlear implant system according to claim 1, wherein
the bottom cover is a stamped titanium cover.

6. The cochlear implant system according to claim 5, wherein
the stamped titanium cover includes a plurality of feedthroughs.

7. The cochlear implant system according to claim 1, wherein
the main body is made of a biocompatible ceramic material.

8. The cochlear implant system according to claim 7, wherein the biocompatible material includes one of
zirconia toughened alumina,
high purity alumina, and
pure zirconia.

9. The cochlear implant system according to claim 1, wherein
the top surface of the magnet includes two or more ribs and equally manny abutments equally spaced around the outer circumference of the outer edge of the top surface,
the abutments are in contact with a rim of the central cavity when the magnet is fully inserted into the central cavity, and
the ribs are not in contact with the rim of the central cavity.

10. The cochlear implant system according to claim 9, wherein
each rib has a smoothly tapered edge connected to the outer edge of the top surface, and
a void is bounded by the outer edge of the top surface and the rim of the central cavity.

11. The cochlear implant system according to claim 10, further comprising:
a tool for removing the magnet from the central cavity, the tool including
a handle portion,
a second magnet installed on a first end of the handle portion,
blades corresponding to the ribs extending from the first end parallel to a central axis of the handle portion, each blade terminating with a hook, wherein
each blade is insertable in said void,
each hook engages under a respective rib when the handle portion is rotated after insertion of the blades, and
the second magnet attracts the magnet in the central cavity when the hooks engage under the ribs.

12. The cochlear implant system according to claim 1, wherein
the magnet includes
an outer casing made of a biocompatible material, and
a magnetic core.

13. A cochlear implant system, comprising:
a subcutaneous housing containing electronics for at least stimulation or collection of data and at least one antenna for communicating with an external device, the subcutaneous housing including
a main body having a central cavity in a center of the subcutaneous housing formed by a portion of an outer surface of the main body and
a magnet removably inserted into said central cavity, the magnet including
a cylindrical body with a central axis, the central axis aligned with a removal axis of the central cavity, and
a top surface, the top surface including
an outer edge,
a plurality of ribs extending radially farther than the outer edge, and
a plurality of abutments extending radially farther than the ribs,
a tool, for removing the magnet from the central cavity, the tool including
a handle portion,
blades corresponding to the ribs extending from the first end parallel to a central axis of the handle portion, each blade terminating with a hook, wherein each blade is insertable along the outer edge of the top surface, each hook engages under a respective rib when the handle portion is rotated after insertion of the blades to form a stable interconnection between magnet and tool.

14. A cochlear implant system as claimed in claim 13, wherein a second magnet is installed on a first end of the handle portion of the tool, and the second magnet attracts the magnet in the central cavity when the hooks engage under the ribs.

* * * * *